United States Patent [19]

Kimura et al.

[11] Patent Number: 5,436,132
[45] Date of Patent: Jul. 25, 1995

[54] QUANTITATIVE DETERMINATION OF TENASCIN AS GLIOMA MARKER

[75] Inventors: Shigeki Kimura, Aichi; Kinya Washizu, Ibaraki; Jun Yoshida, Aichi, all of Japan

[73] Assignee: Amano Pharmaceutical Co., Ltd., Aichim, Japan

[21] Appl. No.: 139,649

[22] Filed: Oct. 22, 1993

[30] Foreign Application Priority Data

Feb. 13, 1993 [JP] Japan ................ 5-047201

[51] Int. Cl.⁶ ............... G01N 33/543; G01N 33/574
[52] U.S. Cl. ................... 435/7.9; 435/7.23; 435/7.93; 435/7.94; 436/512; 436/518; 436/813
[58] Field of Search ............ 435/7.23, 7.9, 7.93, 435/7.94; 436/518, 528, 531, 548, 64, 813, 512

[56] References Cited

FOREIGN PATENT DOCUMENTS 9204464 3/1992 WIPO .

OTHER PUBLICATIONS

Lightner et al, 1989 Tenascin/hexabrachion in human skin: biochemical identification and localization by light and electron microscopy. J Cell Biol 108: 2483-2493.
Herlyn et al, 1991, Characterization of tenascin secreted by human melanoma cells. Cancer Res. 51: 4853-4858.
Bourdon et al, 1983. Human glioma-mesenchymal extracellular matrix antigen defined by monoclonal antibody. Cancer Res 43: 2796-2805.
Kimura et al, 1993. Determination of tenascin in human serum by the use of a new enzyme immunoassay. Biomed. Res. 14: 203-208.

*Primary Examiner*—David Saunders
*Assistant Examiner*—James L. Grun
*Attorney, Agent, or Firm*—Sughrue, Mion, Zinn, Macpeak & Seas

[57] ABSTRACT

A method of determining tenascin in a cerebrospinal fluid sample by immunoassay, etc. is disclosed. The tenascin level in the cerebrospinal fluid serves as a glioma marker and thus the selective diagnosis of glioma is possible.

10 Claims, 1 Drawing Sheet

QUANTITATIVE DETERMINATION OF TENASCIN AS GLIOMA MARKER

FIELD OF THE INVENTION

This invention relates to a method of quantitative determination of tenascin as a brain tumor marker. More particularly, it relates to a method of quantitative determination of tenascin as a glioma marker which comprises determining tenascin in a cerebrospinal fluid, comparing the obtained tenascin level with a standard level, and taking the confirmed presence of high level tenascin as a diagnostic indication for a glioma.

BACKGROUND OF THE INVENTION

Tenascin is an extracellular glycoprotein which was discovered as an antigen defined by the antibody showing unique staining properties different from that to collagen type V by Chiquet and Fambrough in 1984 in their attempt to prepare a monoclonal antibody against collagen type V (see Journal of Cell Biology, Vol. 98, pp. 1926–1936 & 1937–1946 (1984)).

Tenascin was considered at first to be a carcinoembryonic antigen. Thereafter, several monoclonal antibodies against tenascin were prepared, and development of tenascin in various cancers was examined.

In recent years, existence of tenascin in serum was revealed (see Cancer Research, Vol. 51, pp. 4853–4858 (1991)).

Several methods for quantitatively determining tenascin have hitherto been reported. For example, (1) a method for determining tenascin in the human osteosarcoma tissue and the chicken embryonic brain by ELISA using an M1 monoclonal antibody against chicken tenascin and a rabbit polyclonal antibody (see Annals New York Academy of Science, Vol. 580, pp. 260–275 (1990)) and (2) a method comprising mixing the serum of a melanoma-bearing patient and a monoclonal antibody against human tenascin and subsequently reacting the mixture with tenascin bound to a solid phase and determining the monoclonal antibody bound to the tenascin on the solid base after the reaction according to the indirect RIA method (see Cancer Research, Vol. 51, pp. 4853–4858 (1991)) are known.

However, either of these methods is to determine tenascin in plasma or serum and, besides, involves many problems. For example, since method (1) uses antibodies against chicken tenascin and the rate of cross reaction in the measurement of tenascin in human tissues is not established, the result obtained cannot be decided to be an accurate value. According to method (2), the inhibition of binding of antibodies to the tenascin bound to a solid phase by the action of tenascin in the serum sample is merely expressed in terms of percent inhibition so that an accurate amount of tenascin is not obtained.

SUMMARY OF THE INVENTION

In order to solve the above-described problems, the present inventors prepared human tenascin from the culture of human cells, immunized a rat and a rabbit with the resulting human tenascin as an antigen, prepared anti-human tenascin monoclonal antibodies and an anti-human tenascin polyclonal antibody, and prepared reagents for immunoassay using these antibodies, with which a tenascin concentration in the human cerebrospinal fluid can be determined accurately for the first time. At the same time, they found the fact that the tenascin level in a cerebrospinal fluid of a glioma-bearing patient is significantly higher than that in a patient having a benign disease or a patient suffering from an intracranial malignancy other than gliomata. As a result, the inventors have found availability of tenascin as a glioma marker and completed the present invention based on these findings.

The present invention provides a method of selectively detecting the existence as well as the condition of glioma in human by assaying tenascin in a cerebrospinal fluid as a glioma marker. That is, the present invention which determines tenascin as a glioma marker makes it possible to differentiate diagnoses of brain tumors and monitor the glioma in the patient.

The present invention also provides a method of quantitative determination of human tenascin.

DETAILED DESCRIPTION OF THE INVENTION

Figure 1:
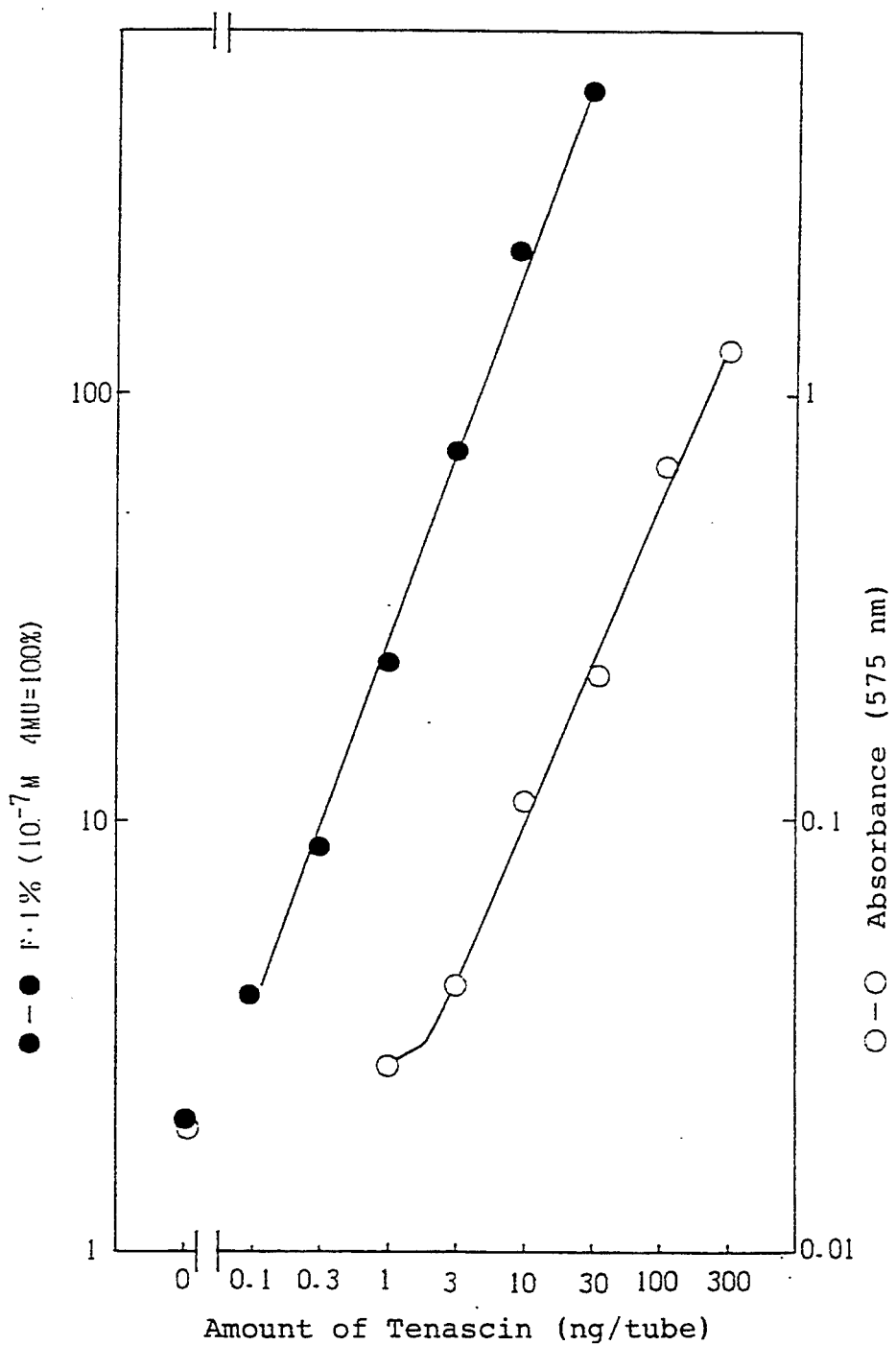
FIGURE 1 is a calibration curve for the sandwich enzyme immunoassay of human tenascin. In the FIGURE, black circles indicate the results in the case of use of a fluorometrical substrate in an enzyme assay, and white circles colorimetrical one, respectively.

According to the present invention, human tenascin can suitably be determined by, for example, an immunoassay using a human tenascin-specific antibody. A typical example of the immunoassay is described below.

Human tenascin can be prepared and purified from human cells by, for example, the process described in JP-A-2-56499 corresponding to EP-A-0434836 (the term "JP-A" as used herein means an "unexamined published Japanese patent application"). An anti-human tenascin antibody is prepared by using the resulting human tenascin as an antigen according to, for example, the process described in JP-A-2-219590.

The anti-human tenascin antibody may be either an immunoglobulin fraction as obtained or the antigen-binding fragment thereof, e.g., an F(ab')$_2$ fragment, an Fab' fragment or an Fab fragment.

Highly purified human tenascin and anti-human tenascin antibody are each bound to a detectable labeling substance to prepare a labelled human tenascin and a labelled anti-human tenascin antibody. The detectable labeling substance should be selected so as to provide sufficient detection sensitivity for human tenascin assaying. Examples of suitable labeling substances include various radioisotopes (preferably, $^{125}$I and $^{131}$I, etc.), various enzymes (preferably, B-D-galactosidase, peroxidase, alkaline phosphatase, glucose oxidase, and malate dehydrogenase, etc.), fluorescent substances (preferably, fluorescein and methylumbelliferone, etc.), and metal ions (preferably, magnesium ion, etc.).

Binding of such a detectable substance to human tenascin or an anti-human tenascin antibody (labeling) can be carried out by any known techniques. For example, labeling with a radioisotope is conducted by using an iodinating reagent, such as chloramine T or Iodogen (produced by Pierce Rockford, Ill. 61105 USA), and labeling with an enzyme is effected by a coupling method using a bifunctional reagent or by a periodate oxidation method.

Other reagents necessary for human tenascin determination include a water-insoluble carrier having an antibody directly bound thereto and an antibody-binding factor to be insolubilized on an water-insoluble carrier. Because the antibody is immunoglobulin, the factor binding thereto is an anti-immunoglobulin antibody, namely a second antibody. In addition, immunoglobulin-binding proteins, such as protein A and protein G of bacteria origin, may also be used as an antibody-binding factor. It is preferable to highly purify these binding factors by affinity chromatography or the like means to increase the antibody-binding capacity. The water-insoluble carrier for insolubilizing the antibody-binding factor includes particles, beads, test tubes, and other small containers made of various polysaccharide gels, synthetic resins (e.g., polystyrene), or those made of glass or metals, and synthetic membranes made of nitrocellulose or nylon.

Tenascin in a cerebrospinal fluid can be assayed using these reagents as follows.

A cerebrospinal fluid which can be collected from the patient by the conventional method is used as a sample with or without dilution.

A predetermined amount of a cerebrospinal fluid sample is reacted with a water-insoluble carrier having bound thereon an antibody in a predetermined amount of a buffer. A total amount of the reaction system is preferably from 50 to 1000 ul. It is preferable to use a buffer containing 0.01 to 1% (w/v, based on the total volume of the buffer) of at least one protein, such as albumin or gelatin and having a pH of from 4 to 8.5. A preferred reaction temperature is from 2° to 40° C.

The reaction time is an important factor affecting on determination sensitivity and, with operating convenience being taken into consideration, preferably ranges from 10 minutes to 4 days. Then, labelled human tenascin or a labelled anti-human tenascin antibody is added thereto to further allow the system to react. Preferred reaction temperature and time are the same as in the above reaction, i.e., at 2° to 40° C. for 10 minutes to 4 days.

After the reaction, the water-insoluble carrier is washed with water or an appropriate buffer, and the labeling substance bound to the water-insoluble carrier is determined. The above-mentioned series of operation are conducted using a standard preparation containing a known concentration of human tenascin, and the measured value of the cerebrospinal fluid is compared with that of the standard preparation to obtain the tenascin level in the cerebrospinal fluid sample.

A procedure of the foregoing assay in the case of use of serum as a sample is described in detail, e.g., in *Biomedical Research*, Vol. 14, No. 3, pp. 203–208 (1993). In addition to the above-mentioned immunoassay, known immunological assays, such as a TIA method and a latex agglutination method, can also be used for tenascin determination.

The thus determined tenascin level in the cerebrospinal fluid can be used as an index for detecting glioma in human. For this purpose, it is required to determine tenascin in cerebrospinal fluid samples from glioma patients whose disease has been established clinically, benign patients, and patients bearing an intracranial malignancy other than gliomata by the method of the present invention. Making a comparison between the tenascin levels in glioma patients and those in benign patients and patients bearing other intracranial malignancies, it was confirmed that the tenascin levels of the former patients are significantly higher than those of the latter patients. Accordingly, it is possible to draw an arbitrary baseline between the tenascin levels in patients having a benign disease or an intracranial malignancy other than gliomata and those in glioma patients. Then, a tenascin level of a cerebrospinal fluid sample of a subject having an unknown tenascin concentration is determined according to the present invention, and whether the measured value is above the baseline is decided to judge the possibility of a glioma of the subject.

It has now been revealed that tenascin is found at a high concentration in the cerebrospinal fluid of a glioma patient and that the tenascin level in the cerebrospinal fluid of a patient having a benign disease or an intracranial malignancy other than gliomata is low. That is, a high tenascin level was detected from the cerebrospinal fluid of patients with astrocytoma, glioblastoma, brain-stem glioma, etc. while the tenascin level in the cerebrospinal fluid of patients with a benign disease, such as cerebral infarct, cerebral hemorrhage, meningitis, spondylosis with cervical vertebra deformans, etc., or patients with an intracranial malignancy other than gliomata was low. From this fact, tenascin determination of a patient's cerebrospinal fluid made it possible to judge the possibility of a glioma.

The results of tenascin determination also furnish data for judging efficacy of a treatment given to a glioma patient or for judging the possibility of a relapse or a metastasis.

The present invention will now be illustrated in greater detail with reference to Example, but the present invention should not be construed as being limited thereto. The antigens, antibodies, etc. used in the assays were prepared in accordance with the above-recited literature, *Biomedical Research*, Vol. 14, No. 3, pp. 203–208 (1993).

EXAMPLE 1

1) Enzyme Immunoassay (EIA):

Tenascin was assayed by the EIA method, and the activity of a labeling enzyme was measured by colorimetry, fluorometry, and a luminescence technique. The labeling enzymes and their substrates used are shown in the following Table 1.

TABLE 1

| Labeling Enzyme | Substrate | | |
|---|---|---|---|
| | Colorimetric Technique | Fluorescence Technique | Luminescence Technique |
| peroxidase | o-phenylene-diamine.H$_2$O$_2$ | H$_2$O$_2$.tyramine | H$_2$O$_2$/luminol |
| β-D-galactosidase | o-nitrophenyl-β-D-galactoside Chlorophenol-red-β-D-galactopyranoside | 4-methyl-umbelliferyl-β-D-galactopyranoside | AMPGD* |
| alkaline phosphatase | o-nitrophenyl-phosphate | 4-methyl-umbelliferyl-phosphate | AMPPD** |

Note:
*3-(4-Methoxyspiro[1,2-dioxetane-3,2'-tricyclo[3.3.1.$^{3,7}$]decan]-4-yl)phenyl-β-galactopyranoside
**3-(4-Methoxyspiro[1,2-dioxetane-3,2'-tricyclo[3.3.1.$^{3,7}$]decan]-4-yl)phenylphosphate The sandwich method and the competitive binding method were conducted as the enzyme immunoassay.

1-1) Sandwich Method:

To 10 ul of a cerebrospinal fluid sample under assay were added one polystyrene bead having an antibody bound thereto (diameter: 6.5 mm) and 0.5 ml of a 10 mM sodium phosphate buffer (0.1% BSA, 0.1M NaCl), and the system was allowed to react at 37° C. for 3 hours.

After completion of the reaction, the bead was washed with water, and 0.5 ml of a solution of an enzyme-labeled antibody was added thereto, followed by reacting at 4° C. overnight.

After completion of the reaction, the bead was washed with water, and the amount of the immune complex (antibody-antigen-labeled antibody) on the bead was determined by measuring the enzyme activity at 37° C. The measurements by colorimetry, fluorometry, and a luminescence technique were made for 60 minutes, 30 minutes, and 30 seconds, respectively. The radioactivity was measured with a scintillation counter in the case of use of radioisotopes as a label.

1-2) Competitive Binding Assay:

To 10 ul of a cerebrospinal fluid sample under assay were added one polystyrene bead having an antibody bound thereto (diameter: 6.5 mm) and 0.5 ml of a 10 mM sodium phosphate buffer having dissolved therein enzyme-labeled tenascin, and the system was allowed to react at 37° C. for 3 hours. After completion of the reaction, the bead was washed with water, and the amount of the immune complex (antibody-labeled antigen) was determined by measuring the enzyme activity at 37° C. by colorimetry, fluorometry, and a luminescence technique for 60 minutes, 30 minutes, and 30 seconds, respectively. The radioactivity was measured with a scintillation counter in the case of use of radioisotopes as a label.

2. Measurement of Standard Tenascin:

To 10 ul of a standard human tenascin solution were added one polystyrene bead (diameter: 6.5 mm) to which a rabbit anti-human tenascin polyclonal antibody F(ab')$_2$ fragment and 0.5 ml of a 10 mM sodium phosphate buffer (pH=7.0; 0.1% BSA, 0.1M NaCl), and the system was allowed to react at 37° C. for 3 hours.

After completion of the reaction, the bead was washed with water, and 0.5 ml of a solution of a rat anti-human monoclonal antibody F(ab')$_2$ fragment labeled with B-D-galactosidase (Boehringer Mannheim, Germany) was added thereto, followed by reacting at 4° C. overnight. To the reaction system was added 0.5 ml of a Chlorophenol-red-$\beta$-D-galactopyranoside solution as a color developing substrate or 0.5 ml of a 4-methylumbelliferyl-$\beta$-D-galactopyranoside solution as a fluorescent substrate to allow the system to react at 37° C. for 1 hour or 30 minutes, respectively. The enzyme reaction was ceased by addition of 2 ml of a 1% galactose solution for the colorimetric system or 2 ml of a 0.1M glycine-NaOH buffer (pH=10.3) for the fluorometric system. The absorbance at 575 nm of the colorimetric system was measured, and the fluorescence intensity at 460 nm of the fluorometric system by excitation at 390 nm was measured. The results of the assays on standard human tenascin are shown in FIGURE 1. The determination sensitivity of the colorimetry and the fluorometry was 1 ng/tube and 0.1 ng/tube, respectively.

3. Determination of Tenascin in Cerebrospinal Fluid:

The tenascin level in the cerebrospinal fluid (10 ul) of patients having a benign disease or glioma patients was determined in the same manner as described in 2. above. The enzyme activity was measured by fluorometry, and the fluorescence intensity of each sample was applied to the calibration curve of the Standard tenascin solution to obtain the tenascin level of the sample. As a result, a high tenascin level was detected from the cerebrospinal fluid of the glioma patients as is shown in the following Table 2.

TABLE 2

| Patient | Disease | Tenascin Level (ng/ml) |
|---|---|---|
| A | astrocytoma | 291.3 |
| B | astrocytoma | 1271 |
| C | astrocytoma | 730.6 |
| D | glioblastoma | 1044 |
| E | glioblastoma | 275 |
| F | glioblastoma | 1295.1 |
| G | glioblastoma | 130.4 |
| H | brain-stem glioma | 174.9 |
| I | brain-stem glioma | 576.1 |

To the contrary, the tenascin level was low (100 ng/ml or less) in the cerebrospinal fluid from patients suffering from a benign disease, i.e., spondylosis with cervical vertebra deformans (11 cases), meningitis (10 cases), cerebral infarct (9 cases), cerebellum deformans (6 cases), encephalosclerosis (3 cases), neurosis (2 cases), cerebral hemorrhage (1 case), polyneuritis (1 case), Parkinson's disease (1 case), dementia (1 case), Huntington's disease (1 case), syringomyelia (1 case), bulbar amyotrophia (1 case), etc.

As described above, the present invention makes it possible to determine human tenascin with high accuracy. Comparison of a tenascin level in a body fluid of a subject with that of a standard tenascin preparation lends confirmation to the presence of a high level of tenascin and gives a diagnostic index for a glioma.

While the invention has been described in detail and with reference to specific examples thereof, it will be apparent to one skilled in the art that various changes and modifications can be made therein without departing from the spirit and scope thereof.

What is claimed is:

1. A method of detecting glioma in a patient suspected of having glioma comprising:
    (a) obtaining a sample of cerebrospinal fluid from said patient;
    (b) admixing the sample with an antibody which specifically binds to human tenascin in order to form a complex of said antibody with tenascin present in the sample;
    (c) measuring the amount of complex formed as an indication of the level of tenascin in the sample; and
    (d) comparing the level of tenascin in the sample with a normal level of tenascin determined for samples of cerebrospinal fluid obtained from patients known not to have glioma, wherein an elevated level of tenascin in the sample is indicative of glioma in the patient.

2. The method as in claim 1, wherein said antibody is an antigen-binding fragment of an immunoglobulin fraction selected from the group consisting of an F(ab')$_2$ fragment, an Fab' fragment, and an Fab fragment.

3. The method as in claim 1, wherein said antibody is detectably labeled with a substance selected from the group consisting of a radioisotope, an enzyme, a fluorescent substance, and a metal ion.

4. The method as in claim 3, wherein said radioisotope is selected from the group consisting of $^{125}$I and $^{131}$I.

5. The method as in claim 3, wherein said enzyme is selected from the group consisting of B-D-galactosidase, peroxidase, alkaline phosphatase, glucose oxidase, and malate dehydrogenase.

6. The method as in claim 3, wherein said fluorescent substance is selected from the group consisting of fluorescein and methylumbelliferone.

7. The method as in claim 3, wherein said metal ion is a magnesium ion.

8. The method as in claim 1, wherein said antibody is bound to a water-insoluble carrier.

9. The method as in claim 1, wherein said method is conducted at a reaction temperature of from 2° to 40° C.

10. The method as in claim 1, wherein said method has a reaction time of from 10 minutes to 4 days.

* * * * *